United States Patent [19]

Katopodis

[11] Patent Number: 5,045,453

[45] Date of Patent: Sep. 3, 1991

[54] METHOD FOR DETERMINING SIALIC ACID IN PLASMA

[75] Inventor: Nonda Katopodis, Stamford, Conn.

[73] Assignee: Dianon Systems, Inc., Stamford, Conn.

[21] Appl. No.: 236,891

[22] Filed: Aug. 26, 1988

[51] Int. Cl.$^5$ .......................... C12Q 1/00; G01N 33/48
[52] U.S. Cl. .......................................... 435/18; 435/4;
 435/810; 436/63; 436/64; 436/71; 436/87;
 436/93; 436/129; 436/164; 436/178; 436/813;
 530/420
[58] Field of Search ................... 422/61; 435/4, 810,
 435/18; 436/63, 64, 71, 87, 93, 129, 164, 178,
 813; 530/420

[56] References Cited

U.S. PATENT DOCUMENTS

| | | | |
|---|---|---|---|
| 4,342,567 | 8/1982 | Katopodis et al. | 436/129 |
| 4,520,111 | 5/1985 | Miller | 436/71 X |
| 4,689,755 | 8/1987 | Boute | 364/513 |
| 4,701,418 | 10/1987 | Katopodis | 436/64 |
| 4,748,128 | 5/1988 | Katopodis | 436/93 |
| 4,835,711 | 5/1989 | Hutchins et al. | 364/513 |

FOREIGN PATENT DOCUMENTS 0243200 10/1987 European Pat. Off. ............ 436/129

*Primary Examiner*—Esther L. Kepplinger
*Assistant Examiner*—Carol A. Spiegel
*Attorney, Agent, or Firm*—John P. White

[57] ABSTRACT

The present invention provides a method for extracting lipid bound sialic acid from a sample of blood plasma or serum and determining the amount of sialic acid present in the sample which comprises:

(a) adding to the sample a mixture of a lower alkyl alcohol and a chlorinated lower alkyl hydrocarbon so as to form a resulting admixture, the volume ratio of the lower alkyl alcohol to the chlorinated lower alkyl hydrocarbon being in the range from about 70:30 to about 85:15;

(b) mixing the resulting admixture for a period of time sufficient to dissolve lipid bound sialic acid present in the sample;

(c) treating the admixture so as to form a recoverable, substantially clear lipid bound sialic acid-containing upper phase;

(d) separately recovering from the clear upper phase so formed a predetermined volume of the upper phase; and (e) determining the amount of lipid bound sialic acid present in the predetermined volume of the upper phase and thereby the amount of sialic acid present in the sample.

25 Claims, 2 Drawing Sheets

METHOD FOR DETERMINING SIALIC ACID IN PLASMA

BACKGROUND OF THE INVENTION

This invention concerns an improved method for the determination of sialic acid in plasma or serum which is less time-consuming, less expensive, less variable from sample to sample and less dependent upon the skill and experience of the person performing the test. Much work has been done which indicates that elevated sialic acid content in blood sera of a patient is an indication of the presence of cancer. For example, U.S. Pat. No. 4,146,603 to Davidson, et al. discloses and claims a fairly complex series of procedures whereby elevated sialic acid content is a determinant with respect to cancer specific determinations.

MacBeth and Bekesi, Cancer Res. 22:1170–1176 (1962) measured plasma glycoproteins and found galactose and mannose values were seen in breast cancers without metastases. Kloppel, et al., Proc. Natl. Acad. Sc. 74:3011–3013 (1977) reported 2.5-fold increases of serum sialic acid glycolipids in mice bearing transplantable mammary carcinomas and 2-fold increases in human carcinoma patients. The method involved column chromatographic separation of the gangliosides. A minimum of 1 ml whole blood was required. Kloppel, et al., Am. J. Vet. Res. 39:1377–1380 (1978) also reported increases of sialic acid in 92% of 24 dogs; however, a number of false positives were observed in dogs with other disorders. In leukemic AKR/J mice, Lengle, J. Natl. Cancer Inst. 62:1565–1567 (1979) found increased lipid bound sialic acid in their plasma and thymic lymphocytes. Lipid bound sialic acid levels were found increased in plasma and erythrocytes of humans bearing melanomas. Portoukalian, et al., Biochem. Biophys. Res. Commun. 85:916–920 (1978). Chromatographic separation and purification on columns was followed by evaluation on chromatoplates. Silver, et al., Cancer 41:1497–1499 (1978); Cancer Res. 39:5036–5042 (1979) have reported elevated serum sialic acid values in melanoma patients that were significantly related to the tumor burden. However, 36% of patients with observable tumors showed no elevated serum sialic acid. Hogan-Ryan, et al., Br. J. Cancer 41:587–592 (1980) reporting on total bound serum sialic acid in patients with breast cancer found elevations that corresponded with tumor stage.

One specific method over which the present invention is an improvement is disclosed in the American Association for Cancer Research Annual Meeting PROCEEDINGS Vol 21, March 1980 as Abstract No. 728 by Katopodis, et al. Briefly, this method requires that a 100 $\mu$l plasma sample (reduced to 50 $\mu$l) be extracted with 6 ml of a chloroform/methanol mixture, (2 to 1, volume to volume ratio). The lipid extract is then partitioned with 0.2 of its volume of water. The aqueous phase is evaporated in dryness and the residue redissolved in water. The lipid bound sialic acid is then purified by trichloroacetic acid-phosphotungstic acid precipitation and, after the removal of the supernatant from the resultant precipitate, the precipitate is determined by the Svennerholm and Miettien method (Svennerholm, Quantitative Estimation of Sialic Acid . . . , Biochem. Biophys, Acta 24, pp. 604–611 (1957)).

Another specific method over which the present invention is an improvement is disclosed in Katopodis and Stock, U.S. Pat. No. 4,342,567, issued Aug. 3, 1982. This method is similar to the foregoing but requires only about 50 $\mu$l of sample rather than the 100 $\mu$l required by the prior art method. The drying step is eliminated and there is no use of trichloroacetic acid. Phosphotungstic acid is used alone.

These specific methods suffer from a number of disadvantages including the following: the need for a precisely defined 44.7$\lambda$ starting sample; lipid bound sialic acid is lost during the tube inversion step creating reduced final values; precipitation of the lipid bound sialic acid with phosphotungstic acid is not complete, which is a particular problem when working with samples in which the amount exceeds normal values by only small amounts (e.g., early in cancer development); the rapidity of the test is limited by the 5 minutes waiting time after phosphotungstic acid addition and the cost of the test is not as low as is desirable.

Other methods over which the present invention is an improvement are disclosed in U.S. Pat. No. 4,701,418, issued Oct. 20, 1987 (Katopodis) and U.S. Pat. No. 4,748,128, issued May 31, 1988 (Katopodis). These methods involved the determination of the amount of sialic acid present in the sample by diluting a sample of human whole blood or plasma and then adding a mixture of a chlorinated lower alkyl hydrocarbon, such as chloroform, and a lower alkyl alcohol, such as methanol, mixing the resulting solution, and centrifuging the solution to form a substantially clear upper layer. A protein-precipitating agent is then added to a predetermined volume of the upper layer to precipitate lipid bound sialic acid. The protein precipitating agent disclosed is phosphotungstic acid.

After separating the precipitate from the supernatant, the precipitate is suspended in water and the amount of lipid bound sialic acid is determined by adding a resorcinol reagent and a mixture of butyl acetate and n-butanol and then measuring the absorbance of the resulting solution at 580 nm.

The present invention provides an improved method for determining the amount of sialic acid present in a sample of plasma or serum which in some embodiments is qualitatively and quantitatively more sensitive, and in others at least as sensitive as the methods of the prior art. Moreover, the present invention is more economical, more time efficient, more easily automated, and requires less labor and chemical reagents than the methods of the prior art. The procedure of the present invention differs significantly from known methods in that the present invention has eliminated the necessity for the protein precipitating agent and has reversed the proportions of the lower alkyl alcohol and the chlorinated lower alkyl hydrocarbon in the mixture used for extracting the sialic acid. The prior art discloses a mixture wherein the chlorinated hydrocarbon, typically chloroform, is dominant to the alkyl alcohol, i.e. 2:1 volume ratio. In contrast, the present invention uses a mixture of lower alkyl alcohol and chlorinated lower alkyl hydrocarbon wherein the alcohol to chlorinated hydrocarbon ratio is in the range from about 70:30 to about 85:15. In certain embodiments, the present invention also eliminates the need to use a butyl acetate/n-butanol mixture, which is corrosive and difficult to handle. Table 1 sets forth results obtained by others using the methods of U.S. Pat. No. 4,342,567 and it illustrates the variability obtained when samples from normal subjects were tested.

TABLE I
RESULTS OBTAINED BY DIFFERENT LABORATORIES USING THE METHOD OF U.S. Pat. No. 4,342,567

| NORMAL SAMPLES | | | |
|---|---|---|---|
| RANGE | MEAN | UPPER LIMIT | |
| 15.0–20.0 | 17.5 | 20.0 | (1) |
| 12.8–16.8 | 14.8 | 16.8 | (2) |
| 11.6–19.7 | 15.7 | 19.7 | (3) |
| 11.6–19.1 | 15.4 | 19.1 | (4) |
| 15.0–25.0 | 20.0 | 25.0 | (5) |
| 11.1–15.7 | 13.4 | 15.7 | (6) |
| 16.4–26.6 | 21.5 | 26.6 | (7) |
| NO INFO | 15.3 | NO INFO | (8) |
| NO INFO | NO INFO | 17.2 | (9) |
| 12.6–17.2 | 14.9 | 17.2 | (10) |
| 11.9–26.2 | 19.1 | 26.2 | (11) |
| 15.5–22.5 | 19.0 | 22.5 | (12) |
| 8.7–18.5 | 13.6 | 18.5 | (13) |
| 10.9–18.9 | 14.9 | 18.9 | (14) |
| 10.0–21.0 | 15.5 | 21.0 | (15) |
| MEAN- 12.3–20.6 | 16.4 | 18.2 | |

(1) KATOPODIS AND STOCK, U.S. Pat. No. 4,342,567
(2) CHEN SHU-PAN et al., J. SHANGHAI MED. VOL. 6, 1983
(3) A. M. DNISTRIAN et al., CLINICAL CHEM. 27(10) 1981
(4) S. KAKARI et al., ANTICANCER RES. 4, Suppl. 1:3–6, 1984
(5) L. SANTAMARIA et al., MED. BIOLOGIE ENVIR. VOL. 12, 1984
(6) A. M. DNISTRIAN et al., AACR VOL. 23, 609, 1982
(7) P. KOSMIDIS et al., ASCO, VOL. 2, C-1, 1983
(8) D. MUNJAL et al., FED. PROC., VOL. 42(3), March 1983
(9) K. M. ERBIL et al., CL. CHEM. 29, VOL. 6(194), 1983
(10) CHEN SHU-PAN et al., CHIN. J. OBSTET. & GHY., 18(4):235–38 1983
(11) L. SALVAGNO et al., 13 INTL. CONG. OF CHEMO., 1983 (VIENNA)
(12) L. SALVAGNO et al., I. OF CANCER RESEARCH, 1983
(13) A. K. BHARGAVA et al., ASCO, VOL. 6, No. 2, 1984
(14) S. KAKARI et al., INTL. MEETINGS, SALONICA, GREECE, 1982
(15) T. WUSTROW, GERMAN CANCER CONGRESS, 25/6 GL 1983

SUMMARY OF THE INVENTION

The present invention provides a method for extracting lipid bound sialic acid from a sample of human plasma or serum and determining the amount of lipid bound sialic acid present in the sample which comprises:
(a) adding to the sample a mixture of a lower alkyl alcohol and a chlorinated lower alkyl hydrocarbon so as to form a resulting admixture, the volume ratio of the lower alkyl alcohol to the chlorinated lower alkyl hydrocarbon being in the range from about 70:30 to about 85:15;
(b) mixing the resulting admixture for a period of time sufficient to dissolve lipid bound sialic acid present in the sample;
(c) treating the admixture so as to form a recoverable, substantially clear lipid bound sialic acid-containing upper phase;
(d) separately recovering from the clear upper phase so formed a predetermined volume of the upper phase; and
(e) determining the amount of sialic acid present in the predetermined volume of the upper phase and thereby the amount of lipid bound sialic acid present in the sample.

Another aspect of the invention concerns a method of diagnosing cancer in a human subject which comprises determining the amount of lipid bound sialic acid in a sample of the subject's plasma or serum according to the method of the present invention and comparing the amounts so determined with values obtained for subjects known to have cancer, or alternatively, comparing the amount so determined with values obtained over a period of time for the same subject.

The invention also provides a method for monitoring the progression of cancer in a subject which comprises determining at regular time intervals the amount of lipid bound sialic acid in a sample of the subject's body fluid according to the method of the present invention and comparing the amounts so determined with amounts previously obtained for the subject.

Furthermore, this invention provides a cancer diagnostic kit comprising suitable sample containers in which a test sample is to be placed; sample containers with known amounts of reference samples; a container with a mixture of a lower alkyl alcohol and chlorinated lower alkyl hydrocarbon (75:25 volume ratio); a container of enzymatic solution or resorcinol reagent; a container with a stabilizer buffer solution or a mixture of butyl acetate and n-butanol (85:15 volume ratio); a container of deionized distilled water; and pipettes.

DETAILED DESCRIPTION OF THE INVENTION

The present invention provides a method for extracting lipid bound sialic acid from a sample of plasma or serum and determining the amount of lipid bound sialic acid present in the sample which comprises:
(a) adding to the sample a mixture of a lower alkyl alcohol and a chlorinated lower alkyl hydrocarbon so as to form a resulting admixture, the volume ratio of the lower alkyl alcohol to the chlorinated lower alkyl hydrocarbon being in the range from about 70:30 to about 85:15;
(b) mixing the resulting admixture for a period of time sufficient to dissolve lipid bound sialic acid present in the sample;
(c) treating the admixture so as to form a recoverable, substantially clear lipid bound sialic acid-containing upper phase;
(d) separately recovering from the clear upper phase so formed a predetermined volume of the upper phase; and
(e) determining the amount of lipid bound sialic acid present in the predetermined volume of the upper phase and thereby the amount of lipid bound sialic acid present in the sample.

The amount of lipid bound sialic acid in a sample of plasma or serum may be used as a diagnostic indicator of cancer. The sample typically is recovered from whole blood drawn from a subject and treated using methods described hereinafter to recover the plasma or serum. The plasma or serum may be employed directly.

The volume of the alcohol/chlorinated hydrocarbon mixture added in step (a) is about equal to the volume of the sample. Thus, if the original sample volume is 100μl, the volume of mixture added is about 100μl Suitable chlorinated hydrocarbons include chloroform, methylene chloride, ethylene chloride, propylene chloride and carbon tetrachloride, chloroform being presently preferred. The lower alkyl alcohol may be methanol, ethanol, propanol, n-butanol, isopropanol, isobutanol or isoamyl alcohol. However, the greater the number of carbon atoms in the alcohol, the less effective the mixture is in terms of lipid bound sialic acid extraction. Accordingly, the preferred alcohol is methanol.

Figure 1:
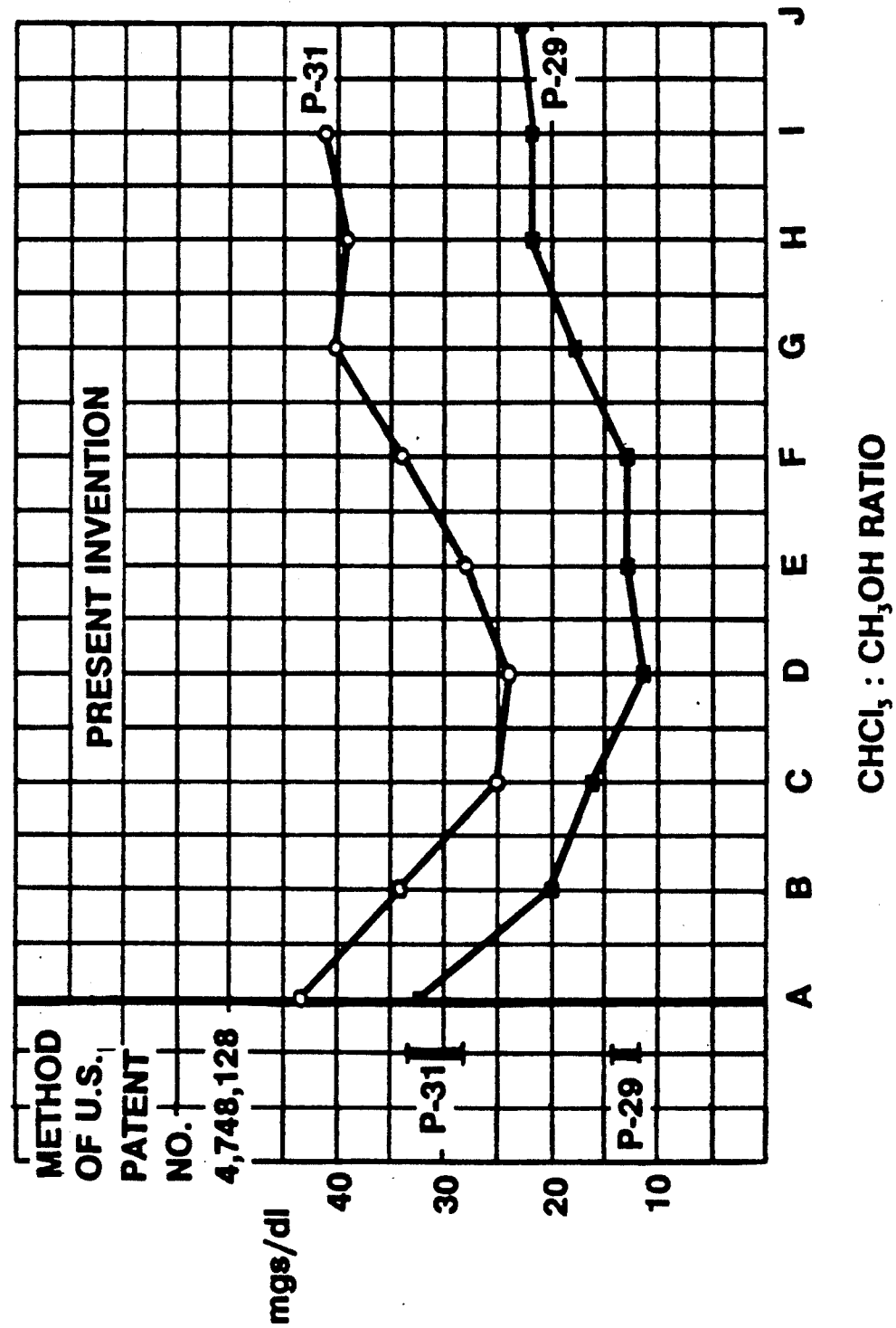
FIG. 1: Comparison of $CHCl_3:CH_3OH$ ratios on the extraction of the supernatant, turbidity of the final color and agreement of the obtained values with those obtained by the method of U.S. Pat. No. 4,748,128

Unlike the alcohol/chlorinated hydrocarbon mixtures used in the methods known in the art, the present invention using a mixture wherein the percentage of alcohol is much greater than the percentage of chlorinated hydrocarbon. The ratios of lower alkyl alcohol:chlorinated lower alkyl hydrocarbon which can be used in the practice of the present invention are between 85:15 and 70:30. In the most preferred embodiment to date, methanol and chloroform are used in a volume ratio of about 75:25. Table 2 and FIG. 1 illustrate the effect of different ratios of alcohol:chlorinated hydrocarbon on the extraction of the supernatant, turbidity of the final color and agreement of the obtained values with those obtained by the methods of the prior art.

TABLE 2

Effect of $CHCl_3:CH_3OH$ Ratio on the Separation of Supernatant (Extract), Turbidity of Final Color and Values Obtained

| # | $CHCl_3:CH_3OH$ mls | POOL #29 mgs/dl | POOL #31 mgs/dl | EXTRACT | TURBIDITY | REMARKS |
|---|---|---|---|---|---|---|
| A | 0–100 | 33.2 | 43.4 | Not Clear | Positive | |
| B | 5–95 | 22.3 | 34.4 | " | " | |
| C | 10–90 | 16.1 | 25.1 | " | " | |
| D | 15–85 | 11.2 | 24.2 | Clear | " | values of |
| E | 20–80 | 13.3 | 28.2 | Clear | Negative | these ratios |
| F | 25–75 | 13.0 | 34.1 | Very Clear | " | agree with the |
| G | 30–70 | 17.7 | 40.0 | " | " | values obtained |
| H | 35–65 | 21.7 | 39.4 | " | " | by the method |
| I | 35–65 | 21.7 | 39.4 | " | " | of U.S. Pat. No. |
| J | 45–55 | 22.8 | N.A. | " | " | 4,748,128 |

The resulting admixture of step (a) is mixed for a suitable period of time to dissolve matter present in the sample in the alcohol/chlorinated hydrocarbon mixture, preferably by gentle interrupted vortexing for about 10 seconds.

The admixture is then treated to permit formation of a recoverable, substantially clear upper phase. Treating may be effected by allowing the mixture to stand or by centrifugation. Preferably, the mixture is centrifuged for at least about two minutes at above 2000 rpm (750 xg) to yield a substantially clear upper phase. In the preferred embodiment, centrifugation is for about 10 minutes at above 3000 rpm.

A predetermined volume of the upper phase is then separately recovered from the substantially clear upper phase so formed, preferably by removing the upper phase from the lower phase and discarding the latter. The predetermined volume so recovered will depend upon the volume of the original sample and on the particular method used in step (e) for determining the amount of lipid bound sialic acid present in the predetermined volume. Thus, if the original volume is about 100 μl, the volume of the upper phase separately recovered will be about 50 μl if an enzymatic solution is used in step (e), and 100 μl if a resorcinol reagent is used. The predetermined volume of the upper phase which is separately recovered will also depend upon the convenience of removing a large volume of the upper phase without disturbing the interface or other material in the tube.

The lipid bound sialic acid content of the recovered predetermined volume of the upper phase may be determined by numerous methods. In one embodiment, a suitable enzyme, such as neuraminidase or a combination of enzymes including neuraminidase, is added to the predetermined volume to form a mixture. The volume of enzyme added depends on the type of enzyme and the predetermined volume of the upper phase. Preferably, the volume of the enzyme is twice the predetermined volume. The mixture is then incubated. Typically the incubation is for about 20 minutes at 37° C. After incubation, a stabilizer buffer solution is added to the mixture to form a resulting solution. The solution is mixed and its absorbance is measured at 550 nm. The amount of lipid bound sialic acid present in the sample is determined by comparing the absorbance measured with the absorbance of one or more standard solutions of known lipid bound sialic acid concentration.

Suitable stabilizer buffer solutions for use in the practice of the present invention are well-known to those skilled in the art to which the present invention pertains. In the preferred embodiment, the buffer solution comprises a mixture of phosphate and sodium hydroxide (NaOH) at a temperature of 37° C. and a pH of 7.5. The buffer solution may be prepared by dissolving 2.72 grams of $KH_2PO_4$ in 500 ml. water, adjusting the pH to 7.5 by adding 10N sodium hydroxide (typically, 20–30 drops) and bringing the solution to 37° C. The resulting buffer solution should be stored at 0°–4° C.

In another embodiment, the amount of lipid bound sialic acid is determined by adding to the predetermined volume of the upper phase a suitable volume of resorcinol reagent. The resorcinol reagent is typically a mixture of resorcinol and water. It has unexpectedly been found that the ratios of resorcinol to water which may be used in the practice of the present invention for forming the resorcinol reagent is limited to about 53:47 to about 57:43. A 55:45 ratio of resorcinol to water has been found to be most effective. The resorcinol reagent (about 0.5 ml of resorcinol reagent when the predetermined volume is 100 μl), is mixed with the upper phase and the resulting solution is boiled for 5 minutes, cooled in an ice bath, and then added to about twice said suitable volume of resorcinol reagent (e.g., about 1 ml) of a mixture of butyl acetate and n-butanol (85:15 volume ratio). The resulting solution of the upper phase, resorcinol reagent and butyl acetate/n-butanol is then mixed and centrifuged for about 5 minutes at above about 2000 rpm to form an organic layer. The organic layer is separated and its absorbance is read at 580 nm. The amount of lipid bound sialic acid present in the sample is then calculated by comparing the absorbance measured with the absorbance of one or more standard solutions of known lipid bound sialic acid concentration.

In a similar embodiment, the amount of sialic acid may be determined by adding to the predetermined volume of the upper phase a suitable volume of resorcinol reagent together with twice said volume of resorcinol reagent of distilled water, instead of the mixture of butyl acetate and n-butanol, and measuring the absorbance at 550 nm.

The determination of the amount of lipid bound sialic acid in the sample may be effected by comparison with standard solutions of known amounts of N-acetyl neuraminic acid (NANA) and interpolating the absorbance reading of the sample with those of the standard solutions.

The various steps of sample handling and manipulation in the various embodiments of this invention, e.g. addition of reagents, mixing, recovering aliquot volumes, centrifuging, etc., may be automated, e.g. with a suitably programmed robotic device(s) appropriately interfaced with suitable equipment for effecting the manipulations, e.g. syringes, deliver tubes, centrifuge, vortexer or other mixing apparatus, etc. Similarly the absorbance of light due to the presence of lipid bound sialic acid may be detected automatically with an appropriately programmed detection apparatus, e.g. a spectrophotomer, suitably interfaced with the robotic device(s). Likewise, the amount of lipid bound sialic acid may be calculated directly from the absorbance so detected using a suitably programmed computer, e.g. microcomputer, appropriately interfaced with the detection device. By automating the method as described above, a reduction in cost per assay and an improvement in the coefficient of variation for the assay may be achieved.

This invention also provides a method of diagnosing cancer in a human subject which comprises determining the amount of lipid bound sialic acid in a sample of the subject's blood plasma or serum according to the method described hereinabove and comparing the amount so determined with values obtained for subjects known to have cancer, or alternatively comparing the amount so determined with values obtained over a period of time for the same subject. Similarly, the invention provides a method of monitoring the progression of cancer in a subject which comprises determining at regular time intervals the amount of lipid bound sialic acid in a sample of the subject's body fluid by the method of the present invention and comparing the amount so determined with amounts previously obtained for the subject. The method may also be used to monitor the response of a patient to therapy or monitor for recurrence of cancer. The method also provides diagnostic information which may be used for determining a treatment program of a cancer patient.

Furthermore, this invention provides a cancer diagnostic kit comprising suitable sample containers in which a test sample may be placed; containers with known amounts of reference samples and/or N-acetyl reuraminic acid standards; a container with a mixture of lower alkyl alcohol and chlorinated lower alkyl hydrocarbon (75:25 volume ratio); a container of enzymatic solution or resorcinol reagent; a container with a stabilizer buffer solution or a mixture of butyl acetate and n-butanol (85:15 volume ratio), if needed; deionized distilled water in a container and pipette tips.

The examples which follow are set forth to aid in an understanding of the invention but are not intended to, and should not be construed to, limit in any way the invention as set forth in the claims which follow thereafter.

EXAMPLE 1

PLASMA COLLECTION

Whole blood is collected in a vacutainer (purple cap) with liquid EDTA (Venoject lavender stopper tubes containing 15% EDTA) or microtainer with EDTA coated beads. After mixing by inversion several times, the tubes are centrifuged at 2200 rpm for 10 minutes in a bench-type clinical centrifuge (IEC HN-S-II centrifuge, Damon/International Equipment Co. with an IEC #958 6-position rotor). Aliquots of the separated plasma are either stored at $-20°$ C. for several months before analysis or analyzed fresh.

EXAMPLE 2

FORMATION OF A CLEAR UPPER PHASE

100 μl of a sample of plasma prepared in accordance with Example 1 is placed in a suitable tube or container. An equal volume (100μl) of methanol:chloroform is then added. Chloroform, methanol and other solvents were obtained in Analytical Reagent (AR) grade from Mallinckrodt Inc. The mixture is vortexed (Vortex-Genie ®, Scientific Industries, Inc.) for 10 seconds. The sample is then centrifuged for 10 minutes at 3000-4000 rpm to form a substantially clear upper phase.

EXAMPLE 3

DETERMINATION OF LIPID BOUND SIALIC ACID IN A 100 μl PLASMA SAMPLE

To a borosilicate culture tube transfer 50 μl of the clear supernatant formed in Example 2 with an MLA pipetter and to this add 100 μl of an enzymatic solution comprising neuraminidase and a buffer solution. Place the tube in a 37° C. water bath and incubate for 20 minutes. At the end of incubation add 1 ml stabilizer buffer solution. After a brief mixing let the tube stand at room temperature for 10 minutes. Measure the absorbance at 550 nm within 30 minutes. The amount of the lipid bound sialic acid present in the sample can be calculated by interpolating the absorbance reading obtained from the sample with the absorbance readings obtained from solutions of known concentrations of lipid bound sialic acid.

EXAMPLE 4

ALTERNATIVE METHOD FOR DETERMINATION OF LIPID BOUND SIALIC ACID IN A 100 μl PLASMA SAMPLE

To a borosilicate culture tube transfer 100 μl of the clear supernatant formed in Example 2 with an MLA pipetter and to this add 0.5 ml of resorcinol reagent. The resulting solution is vortexed and then placed in boiling water for 5 minutes. Immediately after boiling the sample is placed in an ice and water bath for 5 minutes. Thereafter, 1.0 ml of butyl acetate and butanol mixture (85:15 v/v) is added, and the sample vortexed and centrifuged for 5 minutes at a speed about 2500 rpm. The absorbance of the organic layer is then measured at 580 nm (Model 34 spectrophotometer, Beckman Instruments, Inc.) and the amount of lipid bound sialic acid determined by the method previously discussed.

EXAMPLE 5

SECOND ALTERNATIVE METHOD FOR DETERMINATION OF LIPID BOUND SIALIC ACID IN A 100 μl PLASMA SAMPLE

To a borosilicate culture tube transfer 100 μl of clear supernatant formed in Example 2 with an MLA pipetter and to this add 0.5 ml of resorcinol reagent. The resulting solution is vortexed and then placed in boiling water for 5 minutes. Immediately after boiling the sample is placed in an ice and water bath for 5 minutes. Thereafter, 1.0 ml of water is added, and the sample vortexed and centrifuged for 5 minutes at a speed about 2500 rpm. The absorbance of the organic layer is then measured at 850 nm (Model 34 spectrophotometer, Beckman Instruments, Inc.) and the amount of lipid bound sialic acid determined as discussed hereinabove.

EXAMPLE 6

RESORCINOL REAGENT

1. Stock Resorcinol solution (2%)

In a 100 ml volumetric flask weigh out 2 grams of resorcinol (SIGMA #R-1000). Fill up to the mark with distilled water. Keep the solution refrigerated in a dark bottle.

2. Cupric sulfate 0.1 M ($CuSO_4 \cdot 5H_2O$ MALLINCKRODT #4844)

In a 100 ml volumetric flask weigh out 2.497 gm of $CuSO_4 \cdot 5H_2O$. Fill up to the mark with distilled water.

3. HCl conc. FISHER Co. #A-144

Preparation of Resorcinol Reagent:

In a 100 ml volumetric flask add:
a) 10.0 ml of 2% stock resorcinol solution
b) 0.25 ml of 0.1 M $CuSO_4$ (Mix)
c) 9.75 ml distilled water (Mix)
d) fill up to the mark with HCl.

Mix, transfer to a dark container and store at 0°–5° C.

EXAMPLE 7

SAMPLE CALCULATIONS OF LIPID BOUND SIALIC ACID CONCENTRATION

A) With one sample of known lipid bound sialic acid concentration:

A sample (POOL) with a known amount of lipid bound sialic acid is analyzed under the same conditions as the sample with an unknown amount of lipid bound sialic acid. If the known sample produces an optical density (O.D.) of "A" and the unknown sample produces an O.D. of "B" then the concentration of lipid bound sialic acid in the unknown sample is:

$$\frac{O.D. \text{ of } B}{O.D. \text{ of } A} \times \text{lipid bound sialic acid concentration of } A$$

EXAMPLE:
O.D. of known A = .084
O.D. of unknown B = .119
known A concentration = 18.6 mgs %

$$\text{then unknown } B \text{ concentration} = \frac{.119 \times 18.6}{.084} = 26.35 \text{ mgs \%}$$

B) With 3 or 4 samples of known lipid bound sialic acid concentrations:

3 or 4 samples (POOLS) of known lipid bound sialic acid concentrations are analyzed together with the unknown sample. A standard curve is produced from the known samples which is linear and the lipid bound sialic acid concentration of the unknown sample can be read from the standard curve.

EXAMPLE 8

Table 3 sets forth a comparison of the results obtained when lipid bound sialic acid values were determined using the procedure described in U.S. Pat. No. 4,748,128 and the procedure of the present invention. As Table 3 clearly indicates the standard deviation observed with the method of this invention is significantly better than that obtained with the prior method.

Figure 2:
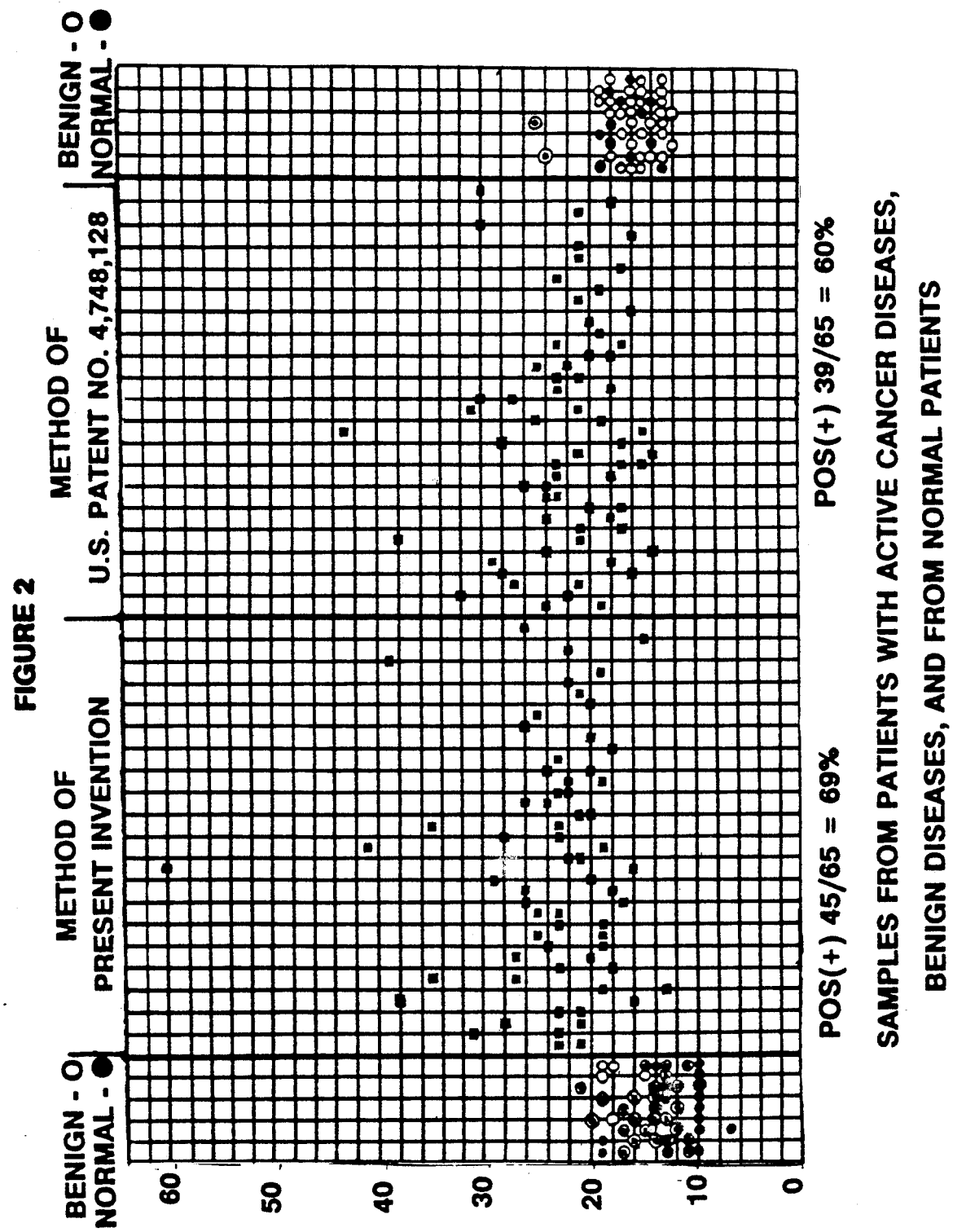
FIG. 2: Comparison of Results Obtained with the method of the present invention and the method of U.S. Pat. No. 4,748,128

FIG. 2 illustrates a comparison of the lipid bound sialic acid values measured in samples from patients with active cancer diseases and benign diseases and from normal patients using the procedure of U.S. Pat. No. 4,748,128 and the procedure of the present invention. As indicated in the figure, the values obtained by the procedure of the present invention had a higher degree of correlation with patients with clinically active diseases than the values obtained by the procedure of U.S. Pat. No. 4,748,128.

TABLE 3

Comparison of Sialic Acid Values by the Procedure of U.S. Pat. No. 4,748,128 and the Procedure of the Present Invention

|  | Pool 29 | | Pool 30 | | Pool 31 | |
| --- | --- | --- | --- | --- | --- | --- |
|  | Previous Procedure[1] | New Procedure[2] | Previous Procedure[1] | New Procedure[2] | Previous Procedure[1] | New Procedure[2] |
| Count | 23 | 11 | 24 | 9 | 18 | 11 |
| Average | 13.08 | 12.66 | 17.23 | 16.67 | 26.43 | 26.71 |
| Std. deviation | 1.01 | 0.67 | 1.89 | 0.76 | 1.56 | 1.34 |
| % std. deviation | 7.7% | 5.3% | 11.0% | 4.5% | 5.9% | 5.0% |

[1] U.S. Pat. No. 4,748,128
[2] by the method of Example 3

What is claimed is:

1. A method for extracting lipid bound sialic acid from a sample of human plasma or serum and determining the amount of lipid bound sialic acid in the sample which comprises:
   (a) adding to the sample a mixture of a lower alkyl alcohol and a chlorinated lower alkyl hydrocarbon so as to form a resulting admixture, the volume ratio of the lower alkyl alcohol to the chlorinated lower alkyl hydrocarbon being in the range from about 70:30 to about 85:15;
   (b) mixing the resulting admixture for a period of time sufficient to dissolve lipid bound sialic acid present in the sample;

(c) treating the admixture so as to form a recoverable, substantially clear lipid bound sialic acid-containing upper phase and a lower phase;

(d) separately recovering from the clear upper phase so formed a predetermined volume of the upper phase; and (e) determining the amount of lipid bound sialic acid present in the predetermined volume of the upper phase and thereby the amount of lipid bound sialic acid present in the sample.

2. A method of claim 1, wherein in step (a) the lower alkyl alcohol is methanol, ethanol, propanol, n-butanol, isopropanol, isobutanol, or isoamyl alcohol.

3. A method of claim 1, wherein in step (a) the chlorinated lower alkyl hydrocarbon is chloroform, methylene chloride, ethylkene chloride, propylene chloride, or carbon tetrachloride.

4. A method of claim 1, wherein in step (a) the lower alkyl alcohol is methanol and the chlorinated lower alkyl hydrocarbon is chloroform.

5. A method of claim 4, wherein the volume ratio of the methanol to the chloroform is about 75:25.

6. A method of claim 1, wherein in the step (b) the mixing comprises vortexing for about 10 seconds.

7. A method of claim 1, wherein in step (c) the treating comprises centrifuging at above about 3000 rpm for at least 10 minutes.

8. A method of claim 1, wherein in step (d) the separately recovering comprises removing the upper phase from the lower phase.

9. A method of claim 1, wherein in step (e) determining the amount of lipid bound sialic acid in the predetermined volume of the upper phase is effected by adding neuraminidase to the predetermined volume to form a mixture, incubating the mixture, adding to the mixture a stabilizer buffer solution to form a resulting solution, mixing the resulting solution, measuring the absorbance due to the presence of sialic acid of the resulting solution at 550 nm, and calculating the amount of lipid bound sialic acid in the sample by comparing the absorbance measured with the absorbance of one or more standard solutions of known lipid bound sialic acid concentration.

10. A method of claim 9, wherein the volume of neuramidinase is twice the predetermined volume of the upper phase.

11. A method of claim 9, wherein the stabilizer buffer solution comprises phosphate and sodium hydroxide at a pH of about 7.5.

12. A method of claim 11, wherein the stabilizer buffer solution is prepared by dissolving $KH_2PO_4$ in water and adding sodium hydroxide to adjust the pH to about 7.5.

13. A method of claim 1, wherein in step (e) determining the amount of lipid bound sialic acid in the predetermined volume of the upper phase is effected by adding a volume of resorcinol reagent to form a solution, mixing the solution, boiling the solution for 5 minutes, cooling the solution in an ice bath, adding to the solution a mixture of about 85:15 volume ratio of butyl acetate and n-butanol in a volume about twice said volume of resorcinol reagent, mixing the resulting solution, centrifuging the resulting solution for about 5 minutes at above about 2000 rpm to form an organic layer, separating the organic layer, reading at 580 nm the absorbance present in the organic layer due to the presence of sialic acid, and calculating the amount of lipid bound sialic acid in the sample by comparing the absorbance measured with the absorbance of one or more standard solutions of known lipid bound sialic acid concentration.

14. A method of claim 1, wherein in step (e) determining the amount of lipid bound sialic acid in the predetermined volume of the upper phase is effected by adding resorcinol reagent to form a solution, mixing the solution, boiling the solution for 5 minutes, cooling the solution in an ice bath, adding water in a volume about twice said suitable volume of resorcinol reagent, mixing the resulting solution, centrifuging the resulting solution for about 5 minutes at above about 2000 rpm, measuring at 580 nm the absorbance of the resulting solution due to the presence of sialic acid, and calculating the amount of lipid bound sialic acid in the sample by comparing the absorbance measured with the absorbance of one or more standard solutions of known lipid bound sialic acid concentration.

15. A method of claim 13 or 14, wherein the resorcinol reagent comprises 55:45 volume ratio of resorcinol to water.

16. A method of claim 13 or 14, wherein the suitable volume of resorcinol reagent is about 0.5 ml.

17. A method of diagnosing cancer in a human subject which comprises determining the amount of lipid bound sialic acid in a sample of the subject's plasma or serum according to the method of claim 1 and comparing the amount so determined with values obtained for samples from subjects known to have cancer.

18. A method of diagnosing cancer in a human subject which comprises determining at regular time intervals the amount of lipid bound sialic acid in a sample of the subject's plasma or serum according to the method of claim 1 and comparing the amounts so determined with amounts previously obtained for samples from the subject.

19. A method of monitoring the progression of cancer in a human subject known to have cancer which comprises determining at regular time intervals the amount of lipid bound sialic acid in a sample of the subject's plasma or serum according to the method of claim 1 and comparing the amount so determined with amounts previously obtained for samples from the subject.

20. A method of monitoring the progression of cancer in a human subject known to have cancer which comprises determining at regular time intervals the amount of lipid bound sialic acid in a sample of the subject's plasma or serum according to the method of claim 9 and comparing the amount so determined with amounts previously obtained for samples from the subject.

21. A cancer diagnostic kit comprising sample containers in which a test sample is to be placed; sample containers with known amounts of a reference sample with a known lipid bound sialic acid concentration; a container with a mixture of lower alkyl alcohol and chlorinated lower alkyl hydrocarbon (75:25 volume ratio); a container of enzymatic solution comprising neuraminidase; a container of stabilizer buffer solution; and pipette tips.

22. A cancer diagnostic kit comprising sample containers in which a test sample is to be placed; sample containers containing known concentrations of lipid bound sialic acid and of N-acetylneuraminic acid as reference standards; a container with a mixture of lower alkyl alcohol and chlorinated lower alkyl hydrocarbon (75:25 volume ratio); a container of resorcinol reagent; a container with a mixture of butyl acetate and n- butanol (85:15 volume ratio); a container of deionized distilled water; and pipette tips.

23. A cancer diagnostic kit comprising sample containers in which a test sample is to be placed; sample containers with known amounts of N-acetylneuraminic acid standards; a container with a mixture of lower alkyl alcohol and chlorinated lower alkyl hydrocarbon (75:25 volume ratio); a container of resorcinol reagent; a container of deionized distilled water; and pipette tips.

24. A method of claim 1, wherein the method is effected in an automated manner using a programmed robotic device(s).

25. A method of claim 9, wherein the method is effected in an automated manner using a programmed robotic device(s).

* * * * *